(12) United States Patent
Manzoni et al.

(10) Patent No.: US 8,679,786 B2
(45) Date of Patent: Mar. 25, 2014

(54) COPPER-ENRICHED BIOMASS, METHOD FOR THE PREPARATION THEREOF AND PRO-BIOTIC, COSMETIC, DIETARY AND NUTRACEUTIC PRODUCTS COMPRISING THE SAME

(75) Inventors: Matilde Manzoni, Milan (IT); Manuela Silvia Rollini, Milan (IT); Alberto Benedetti, Milan (IT)

(73) Assignee: Bioman S.R.L., Turin (IT)

(*) Notice: Subject to any disclaimer, the term of this patent is extended or adjusted under 35 U.S.C. 154(b) by 64 days.

(21) Appl. No.: 13/054,299

(22) PCT Filed: Jul. 15, 2009

(86) PCT No.: PCT/IB2009/053072
§ 371 (c)(1),
(2), (4) Date: Jan. 14, 2011

(87) PCT Pub. No.: WO2010/007586
PCT Pub. Date: Jan. 21, 2010

(65) Prior Publication Data
US 2011/0117604 A1     May 19, 2011

(30) Foreign Application Priority Data

Jul. 16, 2008   (IT) .............................. TO2008A0547

(51) Int. Cl.
*C12P 21/04*   (2006.01)
*C12N 1/00*    (2006.01)

(52) U.S. Cl.
USPC ...................................... 435/71.1; 435/255.2

(58) Field of Classification Search
None
See application file for complete search history.

(56) References Cited

U.S. PATENT DOCUMENTS

2004/0029215 A1*  2/2004  Suenaga et al. .............. 435/68.1
2007/0196536 A1*  8/2007  Andlid et al. .................... 426/12

FOREIGN PATENT DOCUMENTS

GB        724966        2/1955
WO      2006103350 A1  10/2006

OTHER PUBLICATIONS

Mrvcic et al. "Optimization of Bioprocess for Production of Copper-Enriched Biomass of Industrially Important Microorgamism *Saccharomyces cerevisiae*" Journal of Bioscience and Bioengineering, vol. 103, No. 4, 331-337, 2007.*
Fernandes et al. "Modification of plasma membrane lipid order and H+-ATPase activity as part of the response of *Saccharomyces cerevisiae* to cultivation under mild and higher copper stress" Arch Microbiol (2000) 173: 262-268.*

Speisky et al. "Cu(I)-Glutathione complex: A potential source of superoxide readicals generation" Bioorganics and Medicinal Chemistry 16 (2008) 6568-6574.*
Da Costa Ferreira, et al, "Copper(I) transfer into metallothionein mediated by glutathione" Biochemical Journal, vol. 292, No. 3, 1993, pp. 673-676, XP002521866.
Dobrzanski, et al, "The chemical content and feeding value of enriched with chromium, selenium and zinc yeast *Saccharomyces cerevisiae*" Proc. XI Intl. Congress ISAH 2003, 2003, 7 pages., XP002521711.
Freedman, et al., "The Role of Glutathione in Copper Metabolism and Toxicity" Journal of Biological Chemistry, vol. 264, No. 10, 1989, pp. 5598-5605, XP002521867.
Harris, "Cellular copper transport and metabolism." Annual Review of Nutrition 2000, vol. 20, 2000, pp. 291-310, XP002521710.
Mazo, et al., "New food sources of essential trace elements produced by biotechnology facilities" Biotechnology Journal, vol. 2, No. 10, Oct. 2007, pp. 1297-1305, XP009114682.
Mrvcic, et al "Incorporation of copper ions by yeast *Kluyverolmyces marxianus* during cultivation on whey" Acta Alimentaria, vol. 37, No. 1, Mar. 2008, pp. 133-139, XP009114680.
Mrvcic, et al, "Optimization of bioprocess for production of copper-enriched biomass of industrially important microorganism *Saccharomyces cerevisiae*" Journal of Bioscience and Bioengineering, Elsevier, Amsterdam, NL, vol. 103, No. 4, Apr. 1, 2007, pp. 331-337, XP022071900.
Shoeib, et al., "Towards the characterization of metal binding proteins in metal enriched yeast" Microchemical Journal, New York, NY, US, vol. 85, No. 2, Feb. 24, 2007, pp. 329-340, XP005905016.
Stehlik-Tomas, et al., "Zinc, copper and manganese enrichment in yeast *Saccharomyces cerevisae*" Food Technology and Biotechnology, vol. 42, No. 2, Apr. 2004, pp. 115-120, XP009114678.
Dahod, "Raw Materials Selection and Medium Development for Industrial Fermenation Processes," Manual of Industrial Microbiology and Biotechnology, Second Edition, 1999, pp. 213-235, ASM Press, Washington, D.C.

(Continued)

*Primary Examiner* — Blaine Lankford
*Assistant Examiner* — Lauren K Van Buren
(74) *Attorney, Agent, or Firm* — Steinfl & Bruno, LLP

(57) ABSTRACT

The invention relates to a method for the preparation of a copper-enriched biomass, comprising, in a first step, culturing *Saccharomyces cerevisiae* yeast cells in a liquid nutrient medium comprising a carbon source, a nitrogen source, at least one amino acid and a copper salt, so as to obtain copper-enriched yeast biomass in the form of a Cu-GSH complex, wherein the intracellular content of Cu-GSH is higher than 1% dw and, in a second step, separating the copper-enriched yeast biomass from the nutrient liquid medium. Two strains of *Saccharomyces cerevisiae* are described, designated as SA 221 BM and SA 586 BM, respectively (accession numbers DSM 21530 and DSM 21531, deposited with the DSMZ on Jun. 6, 2008), which have the ability to accumulate particularly high levels of intracellular copper. Moreover, the invention relates to the copper-enriched yeast biomass obtainable by the method of the invention, which has an intracellular Cu-GSH content higher than 1% dw, and its use in cosmetic and probiotic products.

10 Claims, No Drawings

(56) References Cited

OTHER PUBLICATIONS

Jimenez, et al., "Effects of Copper Ions on the Free Radical-Scavenging Properties of Reduced Gluthathione: Implications of a Complex Formation," J. Trace Elements Med. Biol., Oct. 2000, vol. 14, pp. 161-167.

Manzoni, M., "Baking Yeasts," Microbiologia Industriale, 2006, pp. 220-224, with English Translation.

Penninckx, M., "A Short Review on the Role of Glutathione in the Response of Yeasts to Nutritional, Environmental, and Oxidative Stresses," Enzyme and Microbial Technology, 2000, vol. 26, pp. 737-742.

Rollini, et al., "Influence of Carbon Source on Glutathione Accumulation in Methylotrophic Yeasts," Annals of Microbiology, 2005, vol. 55, No. 3, pp. 199-203.

Rollini, et al., "Influence of Different Fermentation Parameters on Glutathione Volumetric Productivity by *Saccharomyces cerevisiae*," Process Biochemistry, 2006, vol. 41, pp. 1501-1505.

* cited by examiner

COPPER-ENRICHED BIOMASS, METHOD FOR THE PREPARATION THEREOF AND PRO-BIOTIC, COSMETIC, DIETARY AND NUTRACEUTIC PRODUCTS COMPRISING THE SAME

CROSS REFERENCE TO RELATED APPLICATION(S)

This application is a 35 U.S.C. §371 National Phase Entry Application from PCT/IB2009/053072, filed Jul. 15, 2009, and designating the United States. This application also claims the benefit of Italian Patent Application No. TO2008A000547 filed Jul. 16, 2008, the disclosures of which are incorporated herein in their entirety by reference.

The present invention relates to a copper-enriched biomass and a method for the preparation of a copper-enriched biomass.

The contribution of micro-elements such as copper is very important for the human and animal organism. Copper is an essential element for the cellular energy metabolism, the production of connective tissue and the synthesis of neuro-active peptides. It participates in the respiratory chain, intervenes in hemoglobin synthesis (together with iron) and in the keratinization and pigmentation activity for hair and skin.

However, the delivery of copper within the human and animal organism is made difficult by the toxic effects that such a metal may exert if ingested in high doses.

In order to overcome this problem, the inventors have provided a method for the manufacture of a biomass consisting of yeast cells characterized by a high intracellular copper content in the form of a copper-glutathione complex (Cu-GSH). The biomass obtainable by the method of the invention is hereinbelow referred to as "copper-enriched yeast biomass".

Complexing of copper with glutathione within yeast cells advantageously allows to eliminate the toxicity risks of the metal.

In addition, glutathione itself is a biological molecule useful for the human and animal body. Glutathione (GSH, L-γ-glutamyl-L-cysteinyl-glycine) is in fact the most abundant and widely distributed non-proteinaceous thiol compound within living beings, from prokaryotes to eukaryotes. This tripeptide is intracellulary synthesized by the successive action of two enzymes: the former is γ-glutamylcysteine synthetase (GSH I), which undergoes a feed-back inhibition by GSH itself; the latter is GSH synthase (GSH II). The low redox potential ($E'_0 = -240$ mV) makes GSH a strong cellular redox buffer. In tissues, GSH plays a role of primary importance in bio-reduction mechanisms, protection against oxidative stresses and xenobionts, as well as detoxification from endogenous metabolites, enzymatic activities and the sulfur and nitrogen metabolisms. For these reasons, GSH is considered as a potent and versatile defense molecule. Such features make GSH an important pharmacologically active molecule for treating many pathological conditions, for instance HIV infections, liver cirrhoses, pancreas inflammations, and for counteracting the ageing process. Moreover, GSH is of interest in the food industry and in the field of sports nutrition.

High levels of GSH are found in some yeast species [1, 2] wherein this tripeptide appears to participate in the cellular defense mechanisms against nutritional and oxidative stresses [2, 3].

Furthermore, GSH facilitates the reduction of the copper ion from the $Cu^{++}$ to the $Cu^+$ form. Accordingly, GSH sequestrates $Cu^+$ ions in the form of copper-glutathione conjugates (Cu-GSH). Several studies suggest that the Cu-GSH conjugates play an essential role in transferring copper into the apo-form of copper-containing enzymes (such as superoxide dismutase), of enzymes implicated in the protection of the cell from heavy metal toxicities (such as metallothioneins) and of enzymes implicated in copper transport (such as ceruloplasmin).

The present inventors have solved the above-mentioned problem of the delivery of copper within the human and animal body by finding that yeast *Saccharomyces cerevisiae* cells, if grown in suitable culture conditions, are able to accumulate high concentrations of the Cu-GSH complex within the cell, without such high concentrations resulting deleterious for the survival of the cells.

Based on such finding, the inventors have defined a culture method for yeast *Saccharomyces cerevisiae* cells in a nutrient medium containing a copper salt, under conditions that favor the intracellular accumulation of copper in the form of a Cu-GSH complex.

The copper-enriched yeast biomass obtainable by the method of the invention, which has an intracellular content of the Cu-GSH complex higher than 1% dw, is suitable both for applications in the cosmetic field, for instance for the manufacture of cosmetic or cosmeceutic products, and for applications in the dietary and food field, for instance for the manufacture of products with a probiotic activity, such as food supplements, dietary products, functional foodstuffs, nutraceutic products and various kinds of food preparations.

Thus, a first object of the invention is a method for the preparation of a copper-enriched yeast biomass, characterised by the following steps:

(i) culturing *Saccharomyces cerevisiae* yeast cells in a liquid nutrient medium comprising a carbon source, a nitrogen source, at least one amino acid and one copper salt, so as to obtain a copper-enriched yeast biomass in the form of a Cu-GSH complex wherein the intracellular content of the Cu-GSH complex is higher than 1% dw; and (ii) separating the copper-enriched yeast biomass obtained in the previous step from the liquid nutrient medium.

The method of the invention distinguishes itself for its simplicity and low cost.

The carbon source in the liquid nutrient medium may, for example, comprise sugars such as dextrose, glucose, fructose, saccharose, mannose, mannitol; organic acids; alcohols such as ethanol, glycerol; aldehydes.

The nitrogen source may, for example, comprise malt extract, corn steep liquor, casein enzymatic hydrolysates, amino acids, ammonium salts such as for example ammonium sulfate.

The liquid nutrient medium in which the cells are cultured comprises at least one amino acid, such as for example cysteine, methionine, glutamate, glutamine, glycine, leucine, acetylcysteine, serine, or combinations thereof. The following combinations of amino acids are preferred: cysteine and glycine; cysteine, glycine and serine; cysteine, glycine, serine and methionine.

The copper salt in the liquid nutrient medium is for example copper acetate, sulfate or carbonate. Among these, copper acetate is preferred. The concentration of the copper salt is preferably comprised between 0.1 and 3 mM.

In one preferred embodiment, the liquid nutrient medium comprises one or more further mineral salts in addition to copper acetate, such as for example sodium citrate, potassium sulfate, magnesium sulfate.

In one particularly preferred embodiment, which allows to increase the accumulation of the intracellular Cu-GSH complex, the liquid nutrient medium additionally comprises ATP (adenosine triphosphate) and acetyl phosphate. The preferred concentration of ATP is between 1 and 5 mM, more preferably is 2.5 mM. The preferred concentration of acetyl phosphate is between 5 and 50 mM, more preferably is 20 mM.

The cultivation of the yeast cells in the liquid nutrient medium in order to attain an intracellular Cu-GSH accumulation is carried out at a temperature preferably comprised between 25 and 40° C. and a pH preferably comprised between 3 and 9.

Prior to the passage into the liquid nutrient medium, *Saccharomyces cerevisiae* cells may optionally be pre-cultured under aerobic conditions suitable to favor cell proliferation, with a view to increase the biomass amount. Such growth conditions are well known to the person of skill in the art and are for instance described in [4, 5].

The yeast cells used in the method of the invention are preferably *Saccharomyces cerevisiae* cells in a compressed form, such as those commercially present as baker's yeast. It is more preferred to use an osmo-tolerant yeast, such as the one sold under the commercial name "La Parisienne OSMO", which has the property of resisting to sugar concentrations above 17%. The use of osmo-tolerant yeast allows to obtain a biomass having an intracellular Cu-GSH content higher than 1.5% dw, preferably higher than 2% dw.

By subjecting the osmo-tolerant yeast to adaptation in media with increasing concentrations of copper acetate, the inventors have obtained two strains of osmo-tolerant *Saccharomyces cerevisiae* capable of accumulating particularly high quantities of the Cu-GSH complex within the cell (higher than 2% dw, preferably higher than 3% dw, still more preferably higher than 4% dw) and therefore particularly suitable to be used in the method of the invention. Samples of such strains, designated as SA 221 BM and SA 586 BM, have been deposited under the Budapest Treaty with the *Deutsche Sammlung von Mikroorganismen and Zellkulturen* (DSMZ), located at Inhoffenstr. 7B, D-38124 Braunschweig, Germany, under the accession numbers DSM 21530 and DSM 21531, respectively, on Jun. 6, 2008.

Thus, one preferred embodiment of the method of the invention contemplates the use of yeast *Saccharomyces cerevisiae* cells, strain SA 221 BM (accession number DSM 21530, date of deposit Jun. 6, 2008), or strain SA 586 BM (accession number DSM 21531, date of deposit Jun. 6, 2008).

The examples that follow are provided solely as illustration and are not intended to limit the scope of the invention as defined in the appended claims.

EXAMPLE 1

Yeast cells (*S. cerevisiae*), commercially available as baker's yeast in a compressed form, were resuspended (10% w/v) in a solution containing (g/L): glucose 80, ammonium sulfate 7, magnesium sulfate 0.5, sodium citrate 10, cysteine 4, glycine 4, copper acetate (1.5 and 2.5 mM for comparison). The mixture was incubated at 30° C. in 100-mL flasks, containing 10 ml of the suspension, for a total time of 40 hours. Samples were collected at time intervals of 24, 48 and 72 hours and analyzed for the content of GSH and the Cu-GSH complex.

In order to determine the intracellular concentration of GSH in the reduced and/or Cu-GSH complex form, the cells were subjected to treatment by heat-permeabilization, using the procedure described below [1].

In short, a 1-ml sample was subjected to centrifugation at 10,000 rpm for 10 minutes. The supernatant was subjected to HPLC analysis for determining GSH and the Cu-GSH complex at the extracellular level. The cell pellet was resuspended in 1 ml of ascorbic acid 0.5 g/L in ultrapure HPLC-grade water, treated at 100° C. for 15 minutes, cooled in ice and centrifuged at 12,000 rpm for 12 minutes. The solid residue, consisting of the empty cells, was removed, whilst the permeabilized matter was subjected to HPLC analysis for determining GSH and the Cu-GSH complex at the intracellular level. The quantitative assessment for GSH and the conjugates was performed by using the HPLC system with a 210 nm UV detector, using a (250-4) mm Purospher® end-capped RP-18 column (Merck) thermostated at 30° C., eluted with a 25 mM $NaH_2PO_4$ pH 3.5 solution at 0.3 ml min-1 [6].

The results are set forth in Table 1.

TABLE 1

|  | GSH (% dw) | | | Cu-GSH (% dw) | | |
| --- | --- | --- | --- | --- | --- | --- |
| Cu acetate (mM) | 24 h | 48 h | 72 h | 24 h | 48 h | 72 h |
| Control | 0.1 | 0.8 | 0.9 | — | — | — |
| 1.5 | 0.1 | 0.2 | 0.6 | 0.1 | 1.1 | 1.2 |
| 2.5 | 0.1 | 0.2 | 0.5 | <0.1 | 1.2 | 1.5 |

EXAMPLE 2

Osmo-tolerant yeast *S. cerevisiae* cells in a compressed form (La Parisienne OSMO) were resuspended (10% w/v) in a solution containing (g/L): glucose 80, ammonium sulfate 7, magnesium sulfate 0.5, sodium citrate 10, cysteine 4, glycine 4, copper acetate (0.5 and 1.5 mM for comparison). The mixture was incubated at 30° C. in 100-mL flasks, containing 10 ml of the suspension, for a total time of 72 hours, collecting samples at 24, 48 and 72 hours. The samples were subjected to treatment according to the procedure described in Example 1. The analytical assessment was carried out under the same conditions.

The results are set forth in Table 2.

TABLE 2

|  | GSH (% dw) | | | | Cu-GSH (% dw) | | | |
| --- | --- | --- | --- | --- | --- | --- | --- | --- |
| Cu (mM) | T 0 | 24 h | 48 h | 72 h | T 0 | 24 h | 48 h | 72 h |
| Control | 1.1 | — | — | 1.4 | — | — | — | — |
| 0.5 | 1 | 0.8 | 1.2 | 2.0 | — | 1.0 | 1.8 | 2.1 |
| 1.5 | 1.1 | 0.7 | 1.0 | 1.9 | — | 1.1 | 1.7 | 2.5 |

EXAMPLE 3

Commercial yeast *S. cerevisiae* cells were used at 5% (w/v) in a 20-1 fermenter (15-1 working volume) wherein 2.5 mM ATP and 20 mM acetyl phosphate are added to the reaction solution from Example 1 after a 24-hour reaction. The reaction was performed at 30° C., with aeration at 1 vvm and stirring at 400 rpm.

The results are set forth in Table 3.

TABLE 3

|  | GSH (% dw) | | | | Cu-GSH (% dw) | | | |
| --- | --- | --- | --- | --- | --- | --- | --- | --- |
| Cu (mM) | T 0 | 24 h | 48 h | 72 h | T 0 | 24 h | 48 h | 72 h |
| Control | 0.5 | 0.8 | 1.5 | 1.8 | — | — | — | — |
| 1.5 | 0.5 | 0.9 | 1.6 | 1.7 | — | 1.3 | 1.9 | 2.3 |
| 2.5 | 0.5 | 0.9 | 1.5 | 1.8 | — | 1.4 | 2.0 | 2.7 |

EXAMPLE 4

Yeast SA 221 BM *S. cerevisiae* cells (accession number DSM 21530, filing date Jun. 6, 2008) were grown in a 20-l fermenter (15-l working volume) according to the industrial method (medium containing molasses 80 g/l, ammonium sulfate 8 g/l, magnesium sulfate 0.5 g/l, temperature 30° C., aeration at 1 vvm, stirring at 300 rpm, over-pressure at 0.2 bars). The biomass was collected by centrifugation and then used for the copper-enrichment, using a 5% (w/v) cell concentration and the same procedure as described in Example 2. The samples were subjected to treatment according to the procedure set forth in Example 1. The analytical assessment was carried out under the same conditions.

The results are set forth in Table 4.

TABLE 4

| Cu (mM) | GSH (% dw) | | | Cu-GSH (% dw) | | |
|---|---|---|---|---|---|---|
| | T 0 | 48 h | 72 h | T 0 | 48 h | 72 h |
| Control | 0.4 | 0.5 | 0.6 | — | — | — |
| 0.5 | 0.4 | 0.1 | 0.9 | — | 1.7 | 2.3 |
| 1.5 | 0.4 | 0.9 | 1.3 | — | 2.2 | 3.1 |

Aliquots collected after 72 hours of reaction from the reaction mixture prepared by using 1.5 mM copper salt (3.1% dw Cu-GSH complex), were subjected to cell disruption by sonication, in order to quantify the intracellular copper content by atomic absorption. The procedure used is illustrated herein below. Briefly, a 10-ml sample was subjected to centrifugation at 10,000 for 10 minutes. The cell pellet was resuspended in 5 ml of lysis buffer (Lysis buffer (g/l): 20 mM Tris-HCl, 10 mM $MgCl_2$, 1 mM EDTA, 5% (v/v) glycerol, 0.3 M ammonium sulfate, pH 7.6, ultrapure HPLC-grade water), sonicated in ice for 8 30-second rounds and finally centrifuged at 20,000 rpm for 30 minutes. The cell debris were removed, the permeabilized matter was analyzed by atomic absorption. The atomic absorption analysis showed an intracellular content of 50 μmoles Cu-GSH/ml sample, which corresponds to 1.00 mmole Cu-GSH/g ss.

EXAMPLE 5

Yeast SA 221 BM *S. cerevisiae* cells (accession number DSM 21530, filing date Jun. 6, 2008) were fermented in a 20-l fermenter (15-l working volume) according to the industrial method (medium containing molasses 80 g/l, ammonium sulfate 8 g/l, magnesium sulfate 0.5 g/l, temperature 30° C., aeration at 1 vvm, stirring at 300 rpm, over-pressure at 0.2 bars). The biomass was collected by centrifugation and then used (5% w/v cell content) for the copper-enrichment, using a solution containing (g/l): glucose 80, ammonium sulfate 7, magnesium sulfate 0.5, sodium citrate 10, cysteine 4, glycine 4, serine 4, copper acetate 0.5 and 1.5 mM. 24 hours later, 2.5 mM ATP and 20 mM acetyl phosphate were added. The mixture was incubated at 30° C. in a 15-l fermenter with a 10-l working volume, stirring at 150 rpm, aeration at 1 vvm, while keeping the pH at 6.5, for a total reaction time of 72 hours.

The results are set forth in Table 5.

TABLE 5

| Cu (mM) | GSH (% dw) | | | | Cu-GSH (% dw) | | | |
|---|---|---|---|---|---|---|---|---|
| | T 0 | 24 h | 48 h | 72 h | T 0 | 24 h | 48 h | 72 h |
| Control | 0.9 | — | 1.1 | 1.4 | — | — | — | — |
| 0.5 | 0.9 | 1.1 | 2.0 | 2.4 | — | 1.3 | 2.5 | 3.4 |
| 1.5 | 0.9 | 1.0 | 2.1 | 2.3 | — | 1.5 | 3.1 | 4.2 |

The atomic absorption analysis of the sonicated sample obtained with 1.5 mM Cu after 72 hours of incubation (4.2% dw Cu-GSH) showed an intracellular content of 76 μmoles Cu-GSH/ml sample, corresponing to 1.52 mmoles Cu-GSH/g ss.

EXAMPLE 6

As in Example 5, but with the *Saccharomyces cerevisiae* SA 586 BM yeast (DSM 21531 deposited on Jun. 6, 2008). The results are set forth in Table 6.

TABLE 6

| Cu (mM) | GSH (% dw) | | | | Cu-GSH (% dw) | | | |
|---|---|---|---|---|---|---|---|---|
| | T 0 | 24 h | 48 h | 72 h | T 0 | 24 h | 48 h | 72 h |
| Control | 0.8 | 1.3 | 1.7 | 2.3 | — | — | — | — |
| 1.5 | 0.8 | 1.2 | 1.6 | 2.2 | — | 1.4 | 2.9 | 3.7 |
| 2.5 | 0.8 | 1.2 | 1.7 | 2.1 | — | 1.4 | 3.3 | 4.5 |

EXAMPLE 7

*Saccharomyces cerevisiae* SA 221 BM yeast (DSM 21530 deposited on Jun. 6, 2008). The biomass fermented and collected as in Example 5 is resuspended at 5% (w/v) for copper-enrichment in a 20-l fermenter (15-l working volume) in a solution containing (g/l): glucose 125, lactose 10, ammonium sulfate 7, magnesium sulfate 0.5, sodium citrate 10, cysteine 4, glycine 4, serine 4 and copper acetate 1.5. 24 hours later, 2.5 mM ATP and 20 mM acetyl phosphate are added. Conditions as in Example 5.

The results are set forth in Table 7.

TABLE 7

| Cu (mM) | GSH (% dw) | | | | Cu-GSH (% dw) | | | |
|---|---|---|---|---|---|---|---|---|
| | T 0 | 24 h | 48 h | 72 h | T 0 | 24 h | 48 h | 72 h |
| Control | 0.8 | 1.1 | 1.3 | 1.3 | — | — | — | — |
| 1.5 | 0.8 | 1.0 | 1.4 | 2.4 | — | 1.8 | 3.3 | 4.9 |

BIBLIOGRAPHY

[1] Rollini, M., Pagani, H., Riboldi, S., Manzoni, M. Influence of carbon source on glutathione accumulation in methylotrophic yeasts. Ann Microbiol 2005; 55: 199-203.
[2] Penninckx, M. A short review on the role of glutathione in the response of yeasts to nutritional, environmental, and oxidative stresses. Enz Microb Technol 2000; 26: 737-42.
[3] Rollini, M., Manzoni, M. Influence of different fermentation parameters on glutathione volumetric productivity by *Saccharomyces cerevisiae*. Proc Biochem 2006; 41: 1501-1505.
[4] Manual of Industrial Microbiology and Biotechnology—Second Edition (Demain and Davies ed.), American Society for Microbiology (1999), pp. 213-235.

[5] Manzoni M. Microbiologia Industriale (Edizioni CEA) (2006), pp. 220-224.
[6] Jimenez, I., Speisky, H. Effect of copper ions on the free radical-scavenging properties of reduced glutathione: implications of a complex formation. J Trace Elements Med Biol 2000; 14: 161-7.

The invention claimed is:

1. A method of preparing a copper-enriched yeast biomass, comprising:
   (i) culturing *Saccharomyces cerevisiae* yeast cells of the isolated strain SA 221 BM deposited with the DSMZ under accession number DSM 21530 or of the isolated strain SA 586 BM deposited with the DSMZ under accession number DSM 21531 in a liquid nutrient medium comprising a carbon source, a nitrogen source, at least one amino acid and a copper salt, so as to obtain a copper-enriched yeast biomass in the form of a copper-glutathione (Cu-GSH) complex, wherein the intracellular content of the Cu-GSH complex is higher than 1% dry weight; and
   (ii) separating from the liquid nutrient medium the copper-enriched yeast biomass obtained in step (i).

2. The method according to claim 1, wherein the yeast is osmotolerant *Saccharomyces cerevisiae* in a compressed form.

3. The method according to claim 1, wherein the copper salt is copper acetate.

4. The method according to claim 1, wherein the liquid nutrient medium contains the copper salt at a concentration comprised between 0.1 and 3 mM.

5. The method according to claim 1, wherein the liquid nutrient medium comprises ATP and acetyl phosphate.

6. The method according to claim 1, wherein step (i) is carried out at a temperature comprised between 25 and 40° C. and at a pH comprised between 3 and 9.

7. A copper-enriched biomass, consisting of *Saccharomyces cerevisiae* yeast cells having an intracellular content of the copper-glutathione (Cu-GSH) complex higher than 1% dry weight, wherein the *Saccharomyces cerevisiae* yeast cells are selected from isolated *Saccharomyces cerevisiae* strain SA 221 BM deposited with the DSMZ under accession number DSM 21530 and isolated *Saccharomyces cerevisiae* strain SA 586 BM deposited with the DSMZ under accession number DSM 21531.

8. The biomass according to claim 7, wherein the intracellular content of the Cu-GSH complex is higher than 3% dry weight.

9. A composition having probiotic activity, comprising a biomass according to claim 7.

10. A food preparation, a food supplement, a dietary product, a functional food, a nutraceutic product, a cosmetic product or a cosmeceutic product, comprising a probiotic composition according to claim 9.

* * * * *

UNITED STATES PATENT AND TRADEMARK OFFICE
CERTIFICATE OF CORRECTION

PATENT NO. : 8,679,786 B2                                                        Page 1 of 1
APPLICATION NO. : 13/054299
DATED : March 25, 2014
INVENTOR(S) : Manzoni et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 66 days.

Signed and Sealed this

Twenty-ninth Day of September, 2015

Michelle K. Lee
*Director of the United States Patent and Trademark Office*